United States Patent
Anderhub et al.

(10) Patent No.: US 7,942,896 B2
(45) Date of Patent: May 17, 2011

(54) FORCEPS AND COLLECTION ASSEMBLY AND RELATED METHODS OF USE AND MANUFACTURE

(75) Inventors: Otto E. Anderhub, Miami, FL (US); Christopher D. Endara, Miami, FL (US); Gerardo S. Martin, Hialeah, FL (US); Boris Kesler, Pembroke Pines, FL (US); Osiris A. Nunez, Hollywood, FL (US)

(73) Assignee: Scimed Life Systems, Inc., Maple Grove, MN (US)

( * ) Notice: Subject to any disclaimer, the term of this patent is extended or adjusted under 35 U.S.C. 154(b) by 892 days.

(21) Appl. No.: 10/720,668

(22) Filed: Nov. 25, 2003

(65) Prior Publication Data

US 2005/0113867 A1    May 26, 2005

(51) Int. Cl.
*A61B 17/00* (2006.01)
(52) U.S. Cl. ...................................... 606/207
(58) Field of Classification Search .................. 606/205, 606/51, 116, 117, 184, 207, 52, 206, 208; 600/562, 564; 81/421, 423; 269/257, 258, 269/259, 271
See application file for complete search history.

(56) References Cited

U.S. PATENT DOCUMENTS

| | | | |
|---|---|---|---|
| 30,471 A | 10/1860 | Dudley | |
| 1,609,014 A | * 11/1926 | Dowd | 606/114 |
| 1,615,494 A | 1/1927 | Waring | |
| 1,924,348 A | 8/1933 | Brown | |
| 1,931,740 A | 10/1933 | Ryan | |
| 2,115,298 A | 4/1938 | Brown | |
| 2,131,780 A | 10/1938 | Storz | |
| 2,258,287 A | 10/1941 | Grieshaber | |
| 2,729,210 A | 1/1956 | Spencer | |
| 2,751,908 A | 7/1956 | Wallace | |
| 2,778,357 A | 1/1957 | Leibinger et al. | |
| 3,590,808 A | 7/1971 | Muller | |
| 3,683,892 A | 8/1972 | Harris | |
| 3,844,272 A | 10/1974 | Banko | |
| 3,889,657 A | 6/1975 | Baumgarten | |
| 4,522,206 A | 6/1985 | Whipple et al. | |
| 4,598,710 A | 7/1986 | Kleinberg et al. | |
| 4,632,110 A | 12/1986 | Sanagi | |
| 4,644,951 A | 2/1987 | Bays | |
| 4,651,752 A | 3/1987 | Fuerst | |

(Continued)

FOREIGN PATENT DOCUMENTS

DE    85 32 644.5    5/1986

(Continued)

OTHER PUBLICATIONS

PCT International Search Report and Written Opinion dated Apr. 4, 2005.

*Primary Examiner* — Todd E Manahan
*Assistant Examiner* — Lindsey Bachman
(74) *Attorney, Agent, or Firm* — Finnegan, Henderson, Farabow, Garrett & Dunner LLP

(57) ABSTRACT

An aspect of the invention relates to a forceps and collection assembly having multiple components and their related methods of use and manufacture. More specifically, an embodiment of the invention relates to a forceps for obtaining and collecting multiple samples in a collection assembly, such as a pouch. The forceps has multiple components including an insert cutting edge, a molded biopsy jaw, and an insert molded pouch.

49 Claims, 9 Drawing Sheets

U.S. PATENT DOCUMENTS

| | | | |
|---|---|---|---|
| 4,651,753 A | 3/1987 | Lifton | |
| 4,656,999 A | 4/1987 | Storz | |
| 4,662,371 A | 5/1987 | Whipple et al. | |
| 4,669,471 A | 6/1987 | Hayashi | |
| 4,676,249 A | 6/1987 | Arenas et al. | |
| 4,712,545 A | 12/1987 | Honkanen | |
| 4,721,116 A | 1/1988 | Schintgen et al. | |
| 4,763,668 A | 8/1988 | Macek et al. | |
| 4,763,669 A * | 8/1988 | Jaeger | 600/564 |
| 4,785,825 A | 11/1988 | Romaniuk et al. | |
| 4,815,460 A | 3/1989 | Porat et al. | |
| 4,815,476 A | 3/1989 | Clossick | |
| 4,817,630 A | 4/1989 | Schintgen et al. | |
| 4,880,015 A | 11/1989 | Nierman | |
| 4,887,612 A | 12/1989 | Esser et al. | |
| 4,889,118 A | 12/1989 | Schwiegerling | |
| 4,907,599 A | 3/1990 | Taylor | |
| 4,936,312 A | 6/1990 | Tsukagoshi | |
| 4,950,273 A | 8/1990 | Briggs | |
| 4,953,559 A | 9/1990 | Salerno | |
| 4,971,067 A | 11/1990 | Bolduc et al. | |
| 4,986,279 A | 1/1991 | O'Neill | |
| 4,986,825 A | 1/1991 | Bays et al. | |
| 4,994,024 A | 2/1991 | Falk | |
| 5,037,379 A | 8/1991 | Clayman et al. | |
| 5,052,402 A | 10/1991 | Bencini et al. | |
| 5,059,214 A | 10/1991 | Akopov et al. | |
| 5,074,867 A | 12/1991 | Wilk | |
| 5,082,000 A | 1/1992 | Picha et al. | |
| 5,147,371 A | 9/1992 | Washington et al. | |
| 5,148,813 A | 9/1992 | Bucalo | |
| 5,152,778 A | 10/1992 | Bales, Jr. et al. | |
| 5,161,542 A | 11/1992 | Palestrant | |
| 5,171,256 A | 12/1992 | Smith et al. | |
| 5,172,700 A | 12/1992 | Bencini et al. | |
| 5,176,687 A | 1/1993 | Hasson et al. | |
| 5,183,052 A | 2/1993 | Terwilliger | |
| 5,183,054 A | 2/1993 | Burkholder et al. | |
| 5,188,118 A | 2/1993 | Terwilliger | |
| 5,190,542 A | 3/1993 | Nakao et al. | |
| 5,190,555 A | 3/1993 | Wetter et al. | |
| 5,192,284 A | 3/1993 | Pleatman | |
| 5,192,286 A | 3/1993 | Phan et al. | |
| 5,195,533 A | 3/1993 | Chin et al. | |
| 5,197,968 A | 3/1993 | Clement | |
| 5,201,740 A | 4/1993 | Nakao et al. | |
| 5,217,458 A | 6/1993 | Parins | |
| 5,238,002 A | 8/1993 | Devlin et al. | |
| 5,241,968 A | 9/1993 | Slater | |
| 5,249,582 A | 10/1993 | Taylor | |
| 5,251,641 A | 10/1993 | Xavier | |
| 5,263,967 A | 11/1993 | Lyons, III et al. | |
| 5,267,572 A | 12/1993 | Bucalo | |
| 5,285,795 A | 2/1994 | Ryan et al. | |
| 5,300,087 A | 4/1994 | Knoepfler | |
| 5,316,013 A | 5/1994 | Striebel et al. | |
| 5,330,502 A | 7/1994 | Hassler et al. | |
| 5,341,815 A | 8/1994 | Cofone et al. | |
| 5,342,389 A | 8/1994 | Haber et al. | |
| 5,348,023 A | 9/1994 | McLucas | |
| 5,352,184 A | 10/1994 | Goldberg et al. | |
| 5,354,303 A | 10/1994 | Spaeth et al. | |
| 5,366,467 A | 11/1994 | Lynch et al. | |
| 5,368,597 A | 11/1994 | Pagedas | |
| 5,373,854 A | 12/1994 | Kolozsi | |
| 5,374,227 A | 12/1994 | Webb | |
| 5,374,277 A | 12/1994 | Hassler | |
| 5,383,888 A | 1/1995 | Zvenyatsky et al. | |
| 5,385,570 A | 1/1995 | Chin et al. | |
| 5,396,900 A | 3/1995 | Slater et al. | |
| 5,419,220 A | 5/1995 | Cox | |
| 5,423,854 A | 6/1995 | Martin et al. | |
| 5,449,001 A | 9/1995 | Terwilliger | |
| 5,465,731 A | 11/1995 | Bell et al. | |
| 5,471,992 A | 12/1995 | Banik et al. | |
| 5,476,099 A | 12/1995 | Robinson et al. | |
| 5,478,350 A * | 12/1995 | Kratsch et al. | 606/205 |
| 5,482,054 A * | 1/1996 | Slater et al. | 600/564 |
| 5,511,556 A | 4/1996 | De Santis | |
| 5,535,754 A | 7/1996 | Doherty | |
| 5,538,008 A | 7/1996 | Crowe | |
| 5,542,432 A | 8/1996 | Slater et al. | |
| 5,558,100 A | 9/1996 | Cox | |
| 5,560,373 A | 10/1996 | De Santis | |
| 5,562,102 A | 10/1996 | Taylor | |
| 5,564,436 A | 10/1996 | Hakky et al. | |
| 5,571,129 A | 11/1996 | Porter | |
| 5,573,008 A | 11/1996 | Robinson et al. | |
| 5,595,185 A | 1/1997 | Erlich | |
| 5,601,585 A | 2/1997 | Banik et al. | |
| 5,636,639 A | 6/1997 | Turturro et al. | |
| 5,638,827 A | 6/1997 | Palmer et al. | |
| 5,643,283 A | 7/1997 | Younker | |
| 5,643,307 A * | 7/1997 | Turkel et al. | 606/184 |
| 5,645,075 A | 7/1997 | Palmer et al. | |
| 5,647,372 A | 7/1997 | Tovey et al. | |
| 5,653,713 A | 8/1997 | Michelson | |
| 5,662,671 A | 9/1997 | Barbut et al. | |
| 5,669,394 A | 9/1997 | Bergey et al. | |
| 5,681,324 A | 10/1997 | Kammerer et al. | |
| 5,681,348 A | 10/1997 | Sato | |
| 5,683,359 A | 11/1997 | Farkas et al. | |
| 5,683,388 A | 11/1997 | Slater | |
| 5,683,413 A | 11/1997 | Miyagi | |
| 5,707,392 A * | 1/1998 | Kortenbach | 606/207 |
| 5,720,754 A | 2/1998 | Middleman et al. | |
| 5,735,289 A | 4/1998 | Pfeffer et al. | |
| 5,746,216 A | 5/1998 | Turturro et al. | |
| 5,746,740 A | 5/1998 | Nicholas | |
| 5,759,187 A | 6/1998 | Nakao et al. | |
| 5,762,069 A | 6/1998 | Kelleher et al. | |
| 5,762,070 A | 6/1998 | Nagamatsu | |
| 5,762,613 A | 6/1998 | Sutton et al. | |
| 5,766,177 A | 6/1998 | Lucas-Dean et al. | |
| 5,775,333 A | 7/1998 | Burbank et al. | |
| 5,776,075 A | 7/1998 | Palmer | |
| 5,779,646 A | 7/1998 | Koblish et al. | |
| 5,779,648 A | 7/1998 | Banik et al. | |
| 5,779,716 A | 7/1998 | Cano et al. | |
| 5,795,308 A | 8/1998 | Russin | |
| 5,797,957 A | 8/1998 | Palmer et al. | |
| 5,807,276 A | 9/1998 | Russin | |
| 5,807,277 A | 9/1998 | Swaim | |
| 5,810,744 A | 9/1998 | Chu et al. | |
| 5,810,876 A | 9/1998 | Kelleher | |
| 5,820,630 A | 10/1998 | Lind | |
| 5,823,971 A | 10/1998 | Robinson et al. | |
| 5,840,043 A | 11/1998 | Palmer et al. | |
| 5,840,044 A | 11/1998 | Dassa et al. | |
| 5,843,000 A | 12/1998 | Nishioka et al. | |
| 5,846,248 A | 12/1998 | Chu et al. | |
| 5,848,978 A | 12/1998 | Cecchi | |
| 5,853,374 A | 12/1998 | Hart et al. | |
| 5,871,453 A | 2/1999 | Banik et al. | |
| 5,893,876 A | 4/1999 | Turkel et al. | |
| 5,895,361 A | 4/1999 | Turturro | |
| 5,897,507 A | 4/1999 | Kortenbach et al. | |
| 5,906,621 A | 5/1999 | Secrest et al. | |
| 5,908,437 A | 6/1999 | Asano et al. | |
| 5,919,206 A | 7/1999 | Gengler et al. | |
| 5,928,161 A | 7/1999 | Krulevitch et al. | |
| 5,928,164 A | 7/1999 | Burbank et al. | |
| 5,944,673 A | 8/1999 | Gregoire et al. | |
| 5,957,932 A | 9/1999 | Bates et al. | |
| 5,961,534 A | 10/1999 | Banik et al. | |
| 5,964,716 A | 10/1999 | Gregoire et al. | |
| 5,967,997 A | 10/1999 | Turturro et al. | |
| 5,971,940 A | 10/1999 | Baker et al. | |
| 5,980,468 A | 11/1999 | Zimmon | |
| 6,007,546 A | 12/1999 | Snow et al. | |
| 6,010,512 A | 1/2000 | Chu et al. | |
| 6,013,095 A | 1/2000 | Ouchi | |
| 6,019,733 A | 2/2000 | Farascioni | |
| 6,019,758 A | 2/2000 | Slater | |
| 6,019,770 A | 2/2000 | Christoudias | |
| 6,022,362 A | 2/2000 | Lee et al. | |
| 6,036,698 A | 3/2000 | Fawzi et al. | |

| | | | |
|---|---|---|---|
| RE36,666 E | 4/2000 | Honkanen et al. | |
| 6,050,955 A | 4/2000 | Bryan et al. | |
| 6,053,877 A | 4/2000 | Banik et al. | |
| 6,059,793 A | 5/2000 | Pagedas | |
| 6,068,603 A | 5/2000 | Suzuki | |
| 6,071,233 A | 6/2000 | Ishikawa et al. | |
| 6,071,248 A | 6/2000 | Zimmon | |
| 6,074,408 A | 6/2000 | Freeman | |
| 6,077,230 A | 6/2000 | Gregoire et al. | |
| 6,083,150 A | 7/2000 | Aznoian et al. | |
| 6,083,240 A | 7/2000 | Ouchi | |
| 6,093,195 A | 7/2000 | Ouchi | |
| 6,099,483 A | 8/2000 | Palmer et al. | |
| 6,099,534 A | 8/2000 | Bates et al. | |
| 6,106,553 A | 8/2000 | Feingold | |
| 6,110,127 A | 8/2000 | Suzuki | |
| 6,123,678 A | 9/2000 | Palmer et al. | |
| 6,129,683 A | 10/2000 | Sutton et al. | |
| 6,139,508 A | 10/2000 | Simpson et al. | |
| 6,142,955 A | 11/2000 | Farascioni et al. | |
| 6,142,956 A | 11/2000 | Kortenbach et al. | |
| 6,142,957 A | 11/2000 | Diamond et al. | |
| 6,149,607 A | 11/2000 | Simpson et al. | |
| 6,155,988 A | 12/2000 | Peters | |
| 6,159,162 A | 12/2000 | Kostylev et al. | |
| 6,168,603 B1 | 1/2001 | Leslie et al. | |
| 6,171,315 B1 | 1/2001 | Chu et al. | |
| 6,174,292 B1 | 1/2001 | Kortenbach et al. | |
| 6,174,318 B1 | 1/2001 | Bates et al. | |
| 6,183,482 B1 | 2/2001 | Bates et al. | |
| 6,190,399 B1 | 2/2001 | Palmer et al. | |
| 6,193,671 B1 | 2/2001 | Turturro et al. | |
| 6,206,904 B1 | 3/2001 | Ouchi | |
| 6,224,612 B1 | 5/2001 | Bates et al. | |
| 6,228,095 B1 | 5/2001 | Dennis | |
| 6,231,522 B1 | 5/2001 | Voegele et al. | |
| 6,241,687 B1 | 6/2001 | Voegele et al. | |
| 6,248,081 B1 | 6/2001 | Nishtalas et al. | |
| 6,258,102 B1 | 7/2001 | Pagedas | |
| 6,264,618 B1 | 7/2001 | Landi et al. | |
| 6,264,663 B1 | 7/2001 | Cano | |
| 6,273,860 B1 | 8/2001 | Kostylev et al. | |
| 6,273,861 B1 | 8/2001 | Bates et al. | |
| 6,280,398 B1 | 8/2001 | Ritchart et al. | |
| 6,280,451 B1 | 8/2001 | Bates et al. | |
| 6,283,924 B1 | 9/2001 | Ouchi | |
| 6,299,630 B1 | 10/2001 | Yamamoto | |
| 6,309,404 B1 | 10/2001 | Krzyzanowski | |
| 6,322,522 B1 | 11/2001 | Zimmon | |
| 6,328,701 B1 | 12/2001 | Terwilliger | |
| 6,331,165 B1 | 12/2001 | Turturro et al. | |
| 6,350,266 B1 | 2/2002 | White et al. | |
| 6,368,290 B1 | 4/2002 | Baska | |
| 6,375,661 B2 | 4/2002 | Chu et al. | |
| 6,378,351 B1 | 4/2002 | Ouchi et al. | |
| 6,383,196 B1 | 5/2002 | Leslie et al. | |
| 6,383,197 B1 | 5/2002 | Conlon et al. | |
| 6,387,102 B2 | 5/2002 | Pagedas | |
| 6,409,678 B1 | 6/2002 | Ouchi | |
| 6,409,733 B1 | 6/2002 | Conlon et al. | |
| 6,419,640 B1 | 7/2002 | Taylor | |
| 6,419,679 B1 | 7/2002 | Dhindsa | |
| 6,425,910 B1 | 7/2002 | Hugueny et al. | |
| 6,427,509 B1 | 8/2002 | Ouchi et al. | |
| 6,432,064 B1 | 8/2002 | Hibner et al. | |
| 6,436,054 B1 | 8/2002 | Viola et al. | |
| 6,440,085 B1 * | 8/2002 | Krzyzanowski | 600/564 |
| 6,443,909 B1 | 9/2002 | Ouchi | |
| 6,454,727 B1 | 9/2002 | Burbank et al. | |
| 6,461,310 B1 | 10/2002 | Palmer et al. | |
| 6,468,227 B2 | 10/2002 | Zimmon | |
| 6,485,436 B1 | 11/2002 | Truckai et al. | |
| 6,488,636 B2 | 12/2002 | Bryan et al. | |
| 6,494,885 B1 | 12/2002 | Dhindsa | |
| 6,514,197 B1 | 2/2003 | Ouchi et al. | |
| 6,514,269 B2 | 2/2003 | Yamamoto | |
| 6,517,498 B1 | 2/2003 | Burbank et al. | |
| 6,520,968 B2 | 2/2003 | Bates et al. | |
| 6,527,781 B2 | 3/2003 | Bates et al. | |
| 6,530,891 B2 | 3/2003 | Miller | |
| 6,544,194 B1 | 4/2003 | Kortenbach et al. | |
| 6,551,254 B2 | 4/2003 | Nishtalas et al. | |
| 6,554,850 B1 | 4/2003 | Ouchi et al. | |
| 6,561,988 B1 | 5/2003 | Turturro et al. | |
| 6,565,591 B2 | 5/2003 | Brady et al. | |
| 6,575,977 B1 | 6/2003 | Michelson | |
| 6,589,252 B2 | 7/2003 | McGuckin | |
| 6,607,227 B1 | 8/2003 | Morton | |
| 6,613,068 B2 | 9/2003 | Ouchi | |
| 6,620,111 B2 | 9/2003 | Stephens et al. | |
| 6,626,915 B2 | 9/2003 | Leveillee | |
| 6,632,182 B1 | 10/2003 | Treat | |
| 6,673,092 B1 | 1/2004 | Bacher | |
| 6,685,723 B1 | 2/2004 | Ouchi et al. | |
| 6,689,122 B2 | 2/2004 | Yamamoto | |
| 6,695,791 B2 | 2/2004 | Gonzalez | |
| 6,709,445 B2 | 3/2004 | Boebel et al. | |
| 6,736,781 B2 | 5/2004 | Lee | |
| 6,740,106 B2 | 5/2004 | Kobayashi et al. | |
| 6,743,228 B2 | 6/2004 | Lee et al. | |
| 6,752,822 B2 | 6/2004 | Jespersen | |
| 6,792,663 B2 | 9/2004 | Krzyzanowski | |
| 6,805,699 B2 | 10/2004 | Shimm | |
| 6,808,491 B2 | 10/2004 | Kortenbach et al. | |
| 7,118,586 B1 * | 10/2006 | Paternuosto | 606/205 |
| 2001/0000348 A1 | 4/2001 | Chu et al. | |
| 2001/0009978 A1 | 7/2001 | Krueger et al. | |
| 2001/0047124 A1 | 11/2001 | Yamamoto | |
| 2001/0056248 A1 | 12/2001 | Zimmon | |
| 2002/0013595 A1 | 1/2002 | Yamamoto | |
| 2002/0022850 A1 | 2/2002 | McGuckin, Jr. | |
| 2002/0029006 A1 | 3/2002 | Turturro et al. | |
| 2002/0065474 A1 | 5/2002 | Viola et al. | |
| 2002/0068944 A1 | 6/2002 | White et al. | |
| 2002/0095100 A1 | 7/2002 | Lee et al. | |
| 2002/0111564 A1 | 8/2002 | Burbank et al. | |
| 2002/0120211 A1 | 8/2002 | Wardle et al. | |
| 2002/0143270 A1 | 10/2002 | Miller | |
| 2002/0156395 A1 | 10/2002 | Stephens et al. | |
| 2002/0188220 A1 | 12/2002 | Kryzyzanowski | |
| 2002/0193705 A1 | 12/2002 | Burbank et al. | |
| 2002/0198466 A1 | 12/2002 | Alberico | |
| 2003/0040681 A1 | 2/2003 | Ng et al. | |
| 2003/0073928 A1 | 4/2003 | Kortenbach et al. | |
| 2003/0097147 A1 | 5/2003 | Prestel | |
| 2003/0105402 A1 | 6/2003 | Lee | |
| 2003/0120281 A1 | 6/2003 | Bates et al. | |
| 2003/0125639 A1 | 7/2003 | Fisher et al. | |
| 2003/0163129 A1 | 8/2003 | Lee et al. | |
| 2003/0191413 A1 | 10/2003 | Damarati | |
| 2003/0191464 A1 | 10/2003 | Kidooka | |
| 2003/0212342 A1 | 11/2003 | Rudnick et al. | |
| 2003/0229292 A1 | 12/2003 | Hibner et al. | |
| 2003/0229293 A1 | 12/2003 | Hibner et al. | |
| 2004/0015165 A1 | 1/2004 | Kidooka | |
| 2004/0024333 A1 | 2/2004 | Brown | |
| 2004/0034310 A1 | 2/2004 | McAlister et al. | |
| 2004/0059345 A1 | 3/2004 | Nakao et al. | |
| 2004/0068291 A1 | 4/2004 | Suzuki | |
| 2004/0087872 A1 | 5/2004 | Anderson et al. | |
| 2004/0087979 A1 | 5/2004 | Field et al. | |
| 2004/0097829 A1 | 5/2004 | McRury et al. | |
| 2004/0138587 A1 | 7/2004 | Lyons | |
| 2004/0199159 A1 | 10/2004 | Lee et al. | |
| 2004/0220496 A1 | 11/2004 | Gonzalez | |
| 2004/0254592 A1 | 12/2004 | DiCarlo et al. | |
| 2005/0054945 A1 * | 3/2005 | Cohen et al. | 600/562 |

FOREIGN PATENT DOCUMENTS

| | | |
|---|---|---|
| DE | 8712328 U1 | 3/1988 |
| DE | 8814560 U1 | 3/1989 |
| DE | 3920706 A1 | 1/1991 |
| DE | 4006673 A1 | 9/1991 |
| DE | 9211834 U1 | 4/1993 |
| DE | 68913909 T2 | 10/1994 |
| DE | 695 27 152 T2 | 6/1996 |
| DE | 29614931 U1 | 3/1997 |
| DE | 69310072 T2 | 11/1997 |

| | | | | | | |
|---|---|---|---|---|---|---|
| DE | 69404526 T2 | 12/1997 | | JP | H11-509459 T2 | 8/1999 |
| DE | 69319668 T2 | 12/1998 | | JP | H11-239582 A | 9/1999 |
| DE | 10018674 A1 | 11/2000 | | JP | 2000-279418 A | 10/2000 |
| DE | 10048369 A1 | 4/2001 | | JP | 2000-296131 A | 10/2000 |
| DE | 10048369 C2 | 4/2001 | | JP | 2001-095808 A | 4/2001 |
| DE | 10051651 A1 | 4/2001 | | JP | 2001-112763 A | 4/2001 |
| DE | 10056946 A1 | 5/2001 | | JP | 2001-137998 A | 5/2001 |
| DE | 10128553 A1 | 1/2002 | | JP | 3190029 B2 | 7/2001 |
| DE | 10123848 A1 | 2/2002 | | JP | 2001-517468 A | 10/2001 |
| DE | 10156313 A1 | 6/2003 | | JP | 3220165 B2 | 10/2001 |
| DE | 10316134 A1 | 10/2003 | | JP | 2001-321386 A | 11/2001 |
| DE | 10332613 A1 | 2/2004 | | JP | 2002-011014 A | 1/2002 |
| EP | 0 207 829 A1 | 1/1987 | | JP | 2002-065598 A | 3/2002 |
| EP | 0 207 830 A1 | 1/1987 | | JP | 2003-093393 A | 4/2003 |
| EP | 0 279 358 A2 | 8/1988 | | JP | 2004-000424 A | 1/2004 |
| EP | 0 279 358 B1 | 8/1988 | | JP | 2004-049330 A | 2/2004 |
| EP | 0 380 874 A1 | 8/1990 | | VE | 0 367 818 B1 | 3/1994 |
| EP | 0 585 921 A1 | 3/1994 | | WO | WO 89/10093 A1 | 11/1989 |
| EP | 0 593 929 A1 | 4/1994 | | WO | WO 90/01297 A1 | 2/1990 |
| EP | 0 592 243 B1 | 4/1997 | | WO | WO 94 13215 | 6/1994 |
| EP | 0 621 009 B1 | 7/1997 | | WO | WO 94/26172 A1 | 11/1994 |
| EP | 0 573 817 B1 | 7/1998 | | WO | WO 94/26181 A1 | 11/1994 |
| EP | 0 798 982 B1 | 6/2002 | | WO | WO 95/20914 A1 | 8/1995 |
| EP | 1 240 870 A1 | 9/2002 | | WO | WO 96/19144 A1 | 6/1996 |
| EP | 1 252 863 A1 | 10/2002 | | WO | WO 96/24289 A2 | 8/1996 |
| EP | 1 312 313 A1 | 5/2003 | | WO | WO 97/41776 A1 | 11/1997 |
| EP | 1 348 378 A1 | 10/2003 | | WO | WO 97/41777 A1 | 11/1997 |
| EP | 1 371 332 A1 | 12/2003 | | WO | WO 98/06336 A1 | 2/1998 |
| EP | 1 001 706 B1 | 3/2004 | | WO | WO 98/35615 A1 | 8/1998 |
| JP | S62-049838 A | 3/1987 | | WO | WO 99/07287 A1 | 2/1999 |
| JP | H09-215747 A | 8/1987 | | WO | WO 99/15073 A1 | 4/1999 |
| JP | S62-176438 A | 8/1987 | | WO | WO 99/20096 A2 | 4/1999 |
| JP | H03-139340 A | 6/1991 | | WO | WO 99/53851 A1 | 10/1999 |
| JP | H04-307050 A | 10/1992 | | WO | WO 00/01304 A1 | 1/2000 |
| JP | H05-220157 A | 8/1993 | | WO | WO 00/07502 A1 | 2/2000 |
| JP | H05-237120 A | 9/1993 | | WO | WO 00 33743 | 6/2000 |
| JP | H06-030942 A | 2/1994 | | WO | WO 00/54658 A1 | 9/2000 |
| JP | H06-114063 A | 4/1994 | | WO | WO 01/30242 A1 | 5/2001 |
| JP | H06-189966 A | 7/1994 | | WO | WO 02/39810 * | 5/2002 |
| JP | H06-197906 A | 7/1994 | | WO | WO 02/062226 A1 | 8/2002 |
| JP | H08-206120 A | 8/1996 | | WO | WO 02/062227 A1 | 8/2002 |
| JP | H08-224242 A | 9/1996 | | WO | WO 03/022157 A2 | 3/2003 |
| JP | H09-508561 T2 | 9/1997 | | WO | WO 03/024300 A2 | 3/2003 |
| JP | H09-276282 A | 10/1997 | | WO | WO 03/028557 A1 | 4/2003 |
| JP | 10-099342 | 4/1998 | | WO | WO 03/082119 A1 | 10/2003 |
| JP | H10-137246 A | 5/1998 | | WO | WO 03/082122 A1 | 10/2003 |
| JP | H10-137250 A | 5/1998 | | WO | WO 03/105674 A2 | 12/2003 |
| JP | H10-137251 A | 5/1998 | | WO | WO 2004/010874 A1 | 2/2004 |
| JP | H11-076244 A | 3/1999 | | | | |
| JP | 3220164 B2 | 8/1999 | | * cited by examiner | | |
| JP | H11-509132 T2 | 8/1999 | | | | |

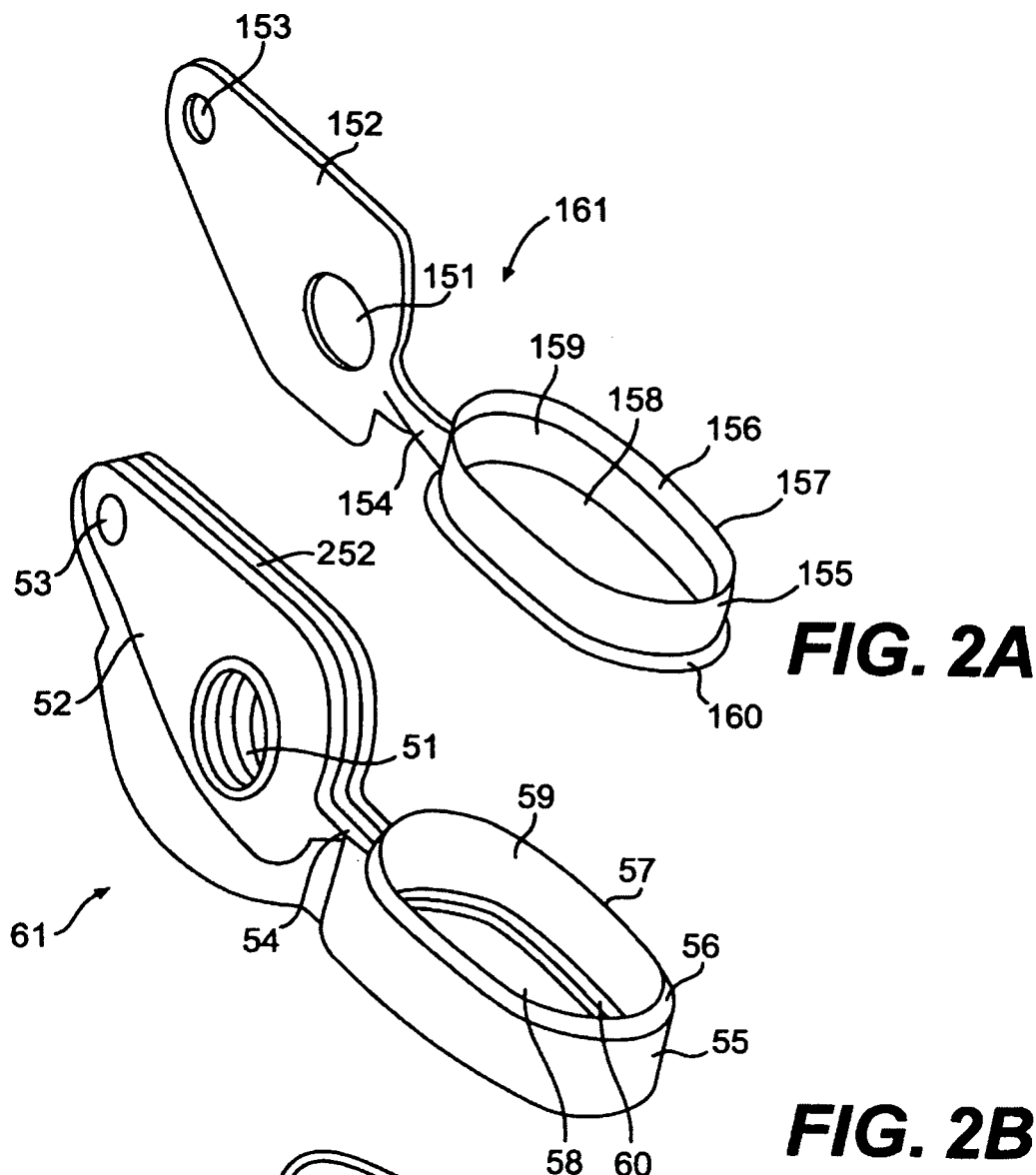
FIG. 2A
FIG. 2B
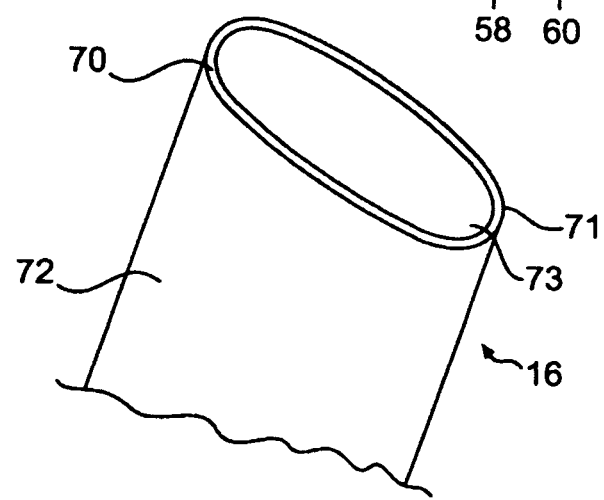
FIG. 2C

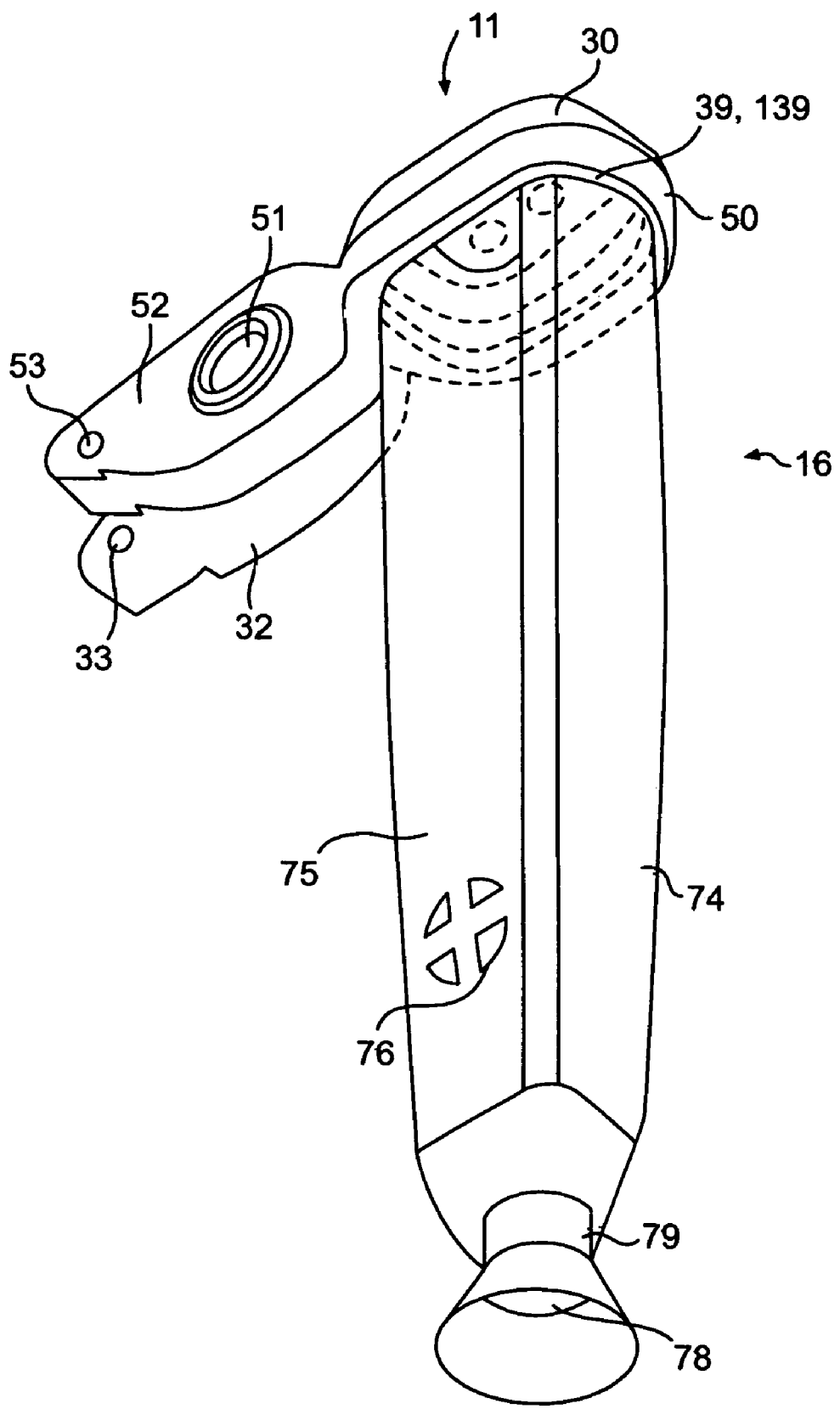

FORCEPS AND COLLECTION ASSEMBLY AND RELATED METHODS OF USE AND MANUFACTURE

FIELD OF THE INVENTION

The invention relates to a forceps and collection assembly and their related methods of use and manufacture. More specifically, in embodiments, the invention relates to a forceps for obtaining and collecting multiple samples in a collection assembly, such as a pouch. The forceps may have multiple components including an insert cutting edge, a molded biopsy jaw, and an insert molded pouch.

BACKGROUND OF THE INVENTION

Irritable bowel disease, Crohn's disease, and Barrett's esophagus are just some of the gastrointestinal diseases that often require biopsy or tissue samples to be taken from the gastrointestinal tract. Often, a large number of biopsy samples must be taken from various locations in the gastrointestinal tract in order to properly diagnose the disease.

Various current biopsy forceps, however, are designed to take only one or two samples in a single pass. Thus, during procedures that require many more tissue samples, up to as many as twenty or more samples in some cases, the forceps must be advanced into and retracted out of the gastrointestinal tract numerous times. Such advancing and retracting of the forceps is time consuming, can cause trauma to the surrounding tissue, and can create sterility issues. Accordingly, a device that minimizes the number of advancements and retractions of the forceps by acquiring and storing multiple biopsy samples in a single pass is desirable. Also desirable is a device that is relatively easy to produce and assemble.

SUMMARY OF THE INVENTION

An embodiment of the invention includes an end effector assembly for obtaining multiple tissue samples comprising a first jaw and a jaw assembly pivotally connected to the first jaw. The jaw assembly includes a cutting portion for mating with the first jaw to cut a tissue sample, a holder, and a storage portion configured to store tissue samples. The holder is configured to receive the cutting portion and the storage portion.

In another embodiment, the invention includes an endoscopic instrument comprising a proximal handle coupled to a distal end effector assembly via an elongate member, the proximal handle for actuating the distal end effector assembly. The distal end effector assembly includes a first jaw and a jaw assembly pivotally connected to the first jaw. The jaw assembly includes a cutting portion for mating with the first jaw to cut a tissue sample, a holder, and a storage portion configured to store tissue samples. The holder is configured to receive the cutting portion and the storage portion.

In yet another embodiment, the invention includes an endoscopic instrument comprising a proximal handle coupled to a distal end effector assembly via an elongate member, the proximal handle for actuating the distal end effector assembly. The distal end effector assembly includes a first end effector and a second end effector assembly pivotally connected to the first end effector. The second end effector assembly includes a second end effector for mating with the first end effector to perform an operation and a holder configured to receive the second end effector.

In a further embodiment, the invention includes a method of manufacturing a cutting device, the method comprising the steps of stamping a first cutting portion, injection molding a holder that receives the first cutting portion, connecting a storage portion to the holder, and pivotally attaching a second cutting portion to the holder, the second cutting portion configured to mate with the first cutting portion to perform cutting.

Various embodiments of the invention may include different features. For example, the holder may have a top configured to receive the cutting portion and a bottom configured to receive the storage portion. In another example, the holder may have a groove for receiving a protrusion on the cutting portion and/or a protrusion on the storage portion. In yet another example, the cutting portion and the holder may be comprised of different materials, such as metals, plastics, rubbers, and/or ceramics. In a further example, the holder may be injection molded around the cutting portion. In still another example, the cutting portion may be inserted into the holder. In a yet further example, the holder and the cutting portion may be formed separately.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

The foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate embodiments of the invention and together with the description, serve to explain the principles of the invention.

FIG. 2A is a perspective view of an insert portion of the lower jaw assembly of the forceps and collection assembly of FIG. 1.

FIG. 2B is a perspective view of a molded portion of the lower jaw assembly of the forceps and collection assembly of FIG. 1.

FIG. 2C is a perspective view of part of a collection pouch of the lower jaw assembly of the forceps and collection assembly of FIG. 1.

FIG. 7 is a perspective view of the jaw assembly of the forceps and collection assembly of FIG. 1.

DESCRIPTION OF THE EMBODIMENTS

Reference will now be made in detail to the present exemplary embodiments of the invention illustrated in the accompanying drawings. Wherever possible, the same reference numbers will be used throughout the drawings to refer to the same or like parts.

Embodiments of the invention relate to a forceps and collection assembly for obtaining and storing multiple tissue samples. Embodiments of the invention also relate to multiple components that comprise the forceps and collection assembly, and their manufacture and assembly. In embodiments that use the forceps and collection assembly in an endoscopic medical procedure, the forceps and collection assembly can be advanced down the working channel of an endoscope and into a tissue tract. When proximate tissue sites, the forceps and collection assembly can obtain and store multiple biopsy samples, and then be retracted from the tissue tract through the working channel of the endoscope.

Figure 1:
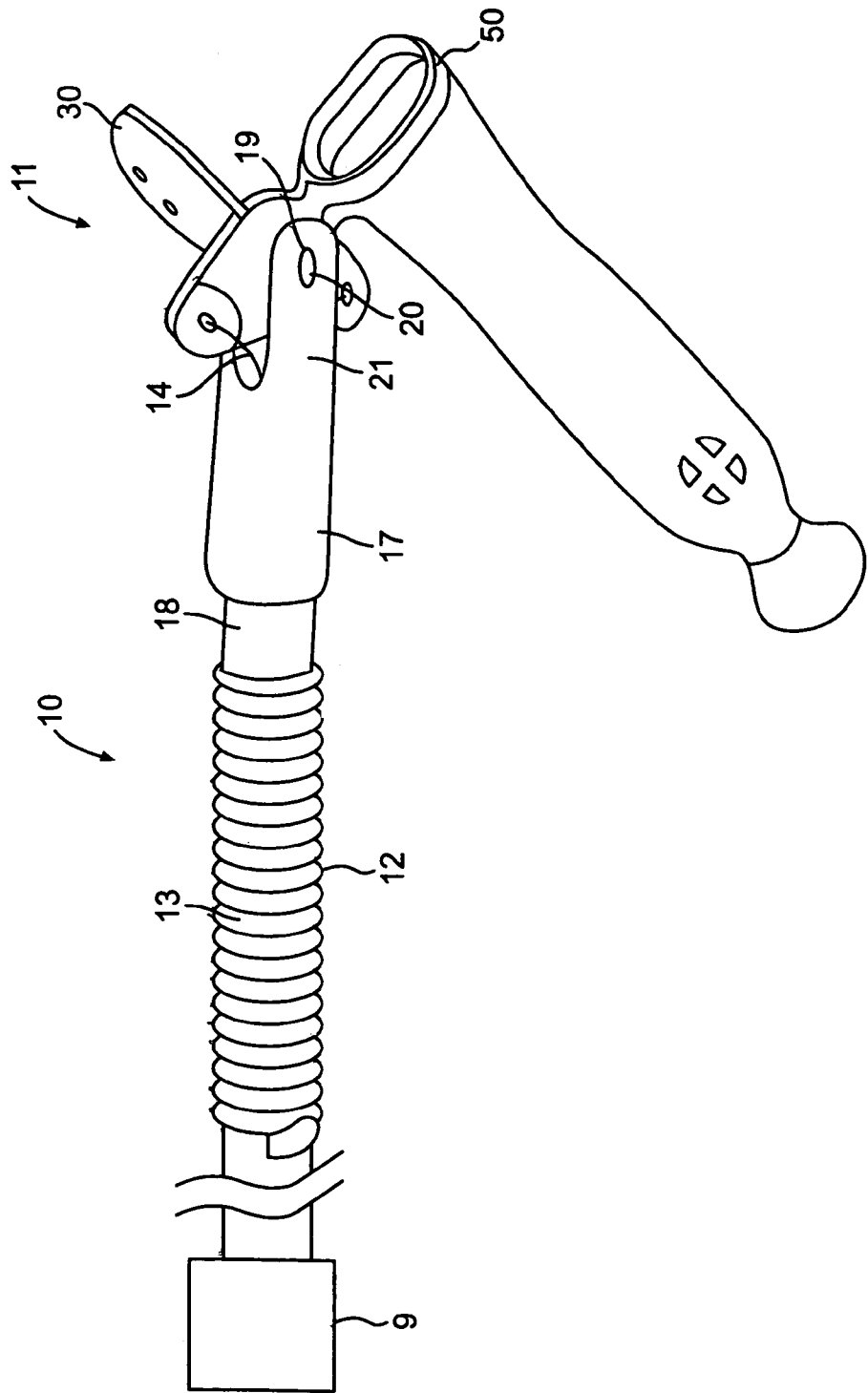
FIG. 1 is a perspective view of a forceps and collection assembly according to an embodiment of the present invention.

An embodiment of a forceps and collection assembly is depicted in FIG. 1. The forceps and collection assembly 10 includes an elongate tubular member 12 that is connected to an endoscopic actuator assembly 9 (i.e. a handle portion) at the proximal end of the assembly 10 and an end effector assembly 11 at a distal end of assembly 10. The endoscopic actuator assembly 9 is shown schematically in FIG. 1 as a box, as assembly 9 may be any suitable handle known in the art that controls the actuation of the end effector assembly 11. Suitable handles may include spool/shaft assemblies, scissor-like handles, or any other known handle used in medical or non-medical applications.

In the embodiment shown in FIG. 1, tubular member 12 includes a flexible helical coil 13 that may include a covering. Any alternative elongate member suitable for medical applications and having sufficient flexibility to traverse tortuous anatomy may be used to connect the proximal actuator assembly 9 to the distal end effector assembly 11.

The main components of end effector assembly 11 include a clevis 17, an upper forceps assembly 30, and a lower forceps assembly 50 having a collection portion in the form of a pouch 16. At its distal end 18, tubular member 12 is connected to upper forceps assembly 30 and lower forceps assembly 50 via clevis 17. The distal end of clevis 17 has a generally U-shaped configuration with a pivot pin 19 extending between pivot holes 20 on opposing pivot arms 21 of the clevis 17. The center of the clevis 17 is hollow and configured to receive pull wires 14 used to actuate the upper forceps assembly 30 and lower forceps assembly 50 located between the pivot arms 21 of the clevis 17. The pull wires 14 connect to upper forceps assembly 30 and lower forceps assembly 50, and extend through clevis 17 and elongate member 12 to the proximal actuation handle 9.

An embodiment of lower forceps assembly 50 is depicted in FIGS. 2A-2C and FIGS. 3A-3B. Lower forceps assembly 50 has a lower molded portion 61, a lower insert portion 161, and a collection pouch 16.

As depicted in the embodiment shown in FIG. 2B, lower molded portion 61 has a pivot bore 51 on the central part of its tang portion 52 that is configured to accommodate pivot pin 19 of clevis 17. Tang portion 52 includes a pull wire hole 53 on its proximal end configured to receive and retain an actuating pull wire 14 from proximal actuation handle 9. Lower molded portion 61 also has central bridging portion 54 that connects proximal tang portion 52 to a cutting edge accommodating portion 55.

Portion 55 includes a cutting edge interface 57 substantially around the inner edge of a top part 56 of a vertical wall 59. Cutting edge interface 57 is configured to accommodate and retain cutting edge 155 of insert portion 161, to be described. A sample receiving hole 58 is in the middle of cutting edge accommodating portion 55, surrounded by vertical wall 59. Along the bottom edge of vertical wall 59 is a holding ring 60. Holding ring 60, which may include one or more recesses and/or protrusions, is configured to facilitate coupling of pouch 16 and lower insert portion 161 to lower molded portion 61, as described in more detail below.

As shown in FIG. 2A, lower insert portion 161 is shaped and configured similar to lower molded portion 61 so that it may be inserted/molded into and retained therein. Lower insert portion 161 has a pivot bore 151 on the central part of a tang portion 152 that is configured to accommodate pivot pin 19 of clevis 17. Tang portion 152 includes a pull wire hole 153 on the proximal end configured to mate with hole 53 and receive and retain the same pull wire 14 received by hole 53. Lower insert portion 161 also has central bridging portion 154 (e.g., twisted portions) that connects the tang portion 152 to cutting edge portion 155. Bridging portion 154 may have any number of planar or non-planar configurations. For example, bridging portion 154 may twist by transitioning from a substantially vertical orientation on the end connected to the tang portion 152, to a substantially horizontal orientation on the end connected to the cutting edge portion 155. As another example, bridging portion 154 may be substantially vertical and have a curved and/or S-shaped configuration between the tank portion and the cutting edge portion 155. Cutting edge 157 is sharp for cutting tissue portions from a tissue tract.

Lower insert portion 161 of lower forceps assembly 50 has a cutting edge portion 155 that includes a cutting edge 157 substantially around the outer edge of a top part 156 of a vertical wall 159. Cutting edge 157 is configured to extend past cutting edge interface 57 of molded portion 61. A sample receiving hole 158 is in the middle of cutting edge portion 155, surrounded by vertical wall 159. Along the bottom outer edge of vertical wall 159 is an interface 160 for coupling portion 161 to molded portion 61 and/or pouch 16. Interface 160 may be a recess configured to receive and retain a protrusion on an upper part of the pouch 16. Alternatively, interface 160 may be a protrusion configured to facilitate coupling of insert portion 161 into a recess in holding ring 60 of molded portion 61 or into a recess of pouch 16.

An embodiment of pouch 16 of the lower forceps assembly 50 is depicted most clearly in FIGS. 1, 2C, and 7. Pouch 16 includes interface portion 70, for example, an outer protrusion along its top rim 71 configured to be received and retained by holding ring 60 of molded portion 61. Extending away from the front rim 71 is base wall 72 defining passage 73 in flow communication with sample receiving holes 58, 158 of lower forceps assembly 50. Passage 73 is configured to receive biopsy samples from lower forceps assembly 50 through sample receiving holes 58, 158.

Base wall 72 extends to a pouch container 74 defining a central cavity 75. Pouch container 74 is substantially cylindrical along its length. Central cavity 75 is in flow communication and substantially axially aligned with both passage 73 and sample receiving holes 58, 158, and is configured to receive and retain the biopsy samples from passage 73. Pouch container 74 has one or more ventilation holes 76 configured to assist in preventing the biopsy samples from sticking to inner wall 77 of pouch container 74, such that the biopsy samples may be more easily pushed into or out of pouch 16 as samples are collected and removed from pouch 16 after assembly 10 is removed from a body. Ventilation holes 76 are configured to prevent such sticking by minimizing the surface area contact between the tissue samples and inner wall 77. Ventilation holes 76 are also configured to allow fluid, for example from the tissue samples, to escape from forceps and collection pouch assembly 10.

At the bottom end of pouch container 74 opposite base wall 72 is flush adapter interface 79 configured to be coupled with a flush adapter. Flush adapters suitable for use in connection with pouch 16 are described in detail in U.S. patent application Ser. No. 10/658,261 filed Sep. 10, 2003, and entitled "A FORCEPS AND COLLECTION ASSEMBLY WITH ACCOMPANYING MECHANISMS AND RELATED METHODS OF USE." The complete disclosure of that patent application is incorporated by reference herein. The flush adapter is configured for use with pouch 16 to aid in removal of tissue samples from the pouch 16. Flush adapter interface 79 has a roughly hourglass shape that defines flush passage 78 that is open at its bottom. Flush adapter interface 79 with flush passage 78 has a restriction that is a narrowed portion of pouch 16. Passage 78 is configured to facilitate flow communication between central cavity 75 of pouch container 74 and the external environment, but prevent biopsy samples from exiting pouch 16 through the bottom of flush passage 78, for example, because it has a smaller cross section than the target sample sizes. Flush passage 78 and the central cavity 75 are substantially axially aligned with each other. Pouch 16 may be made of a plastic or any other suitable biocompatible material.

Figure 4A:
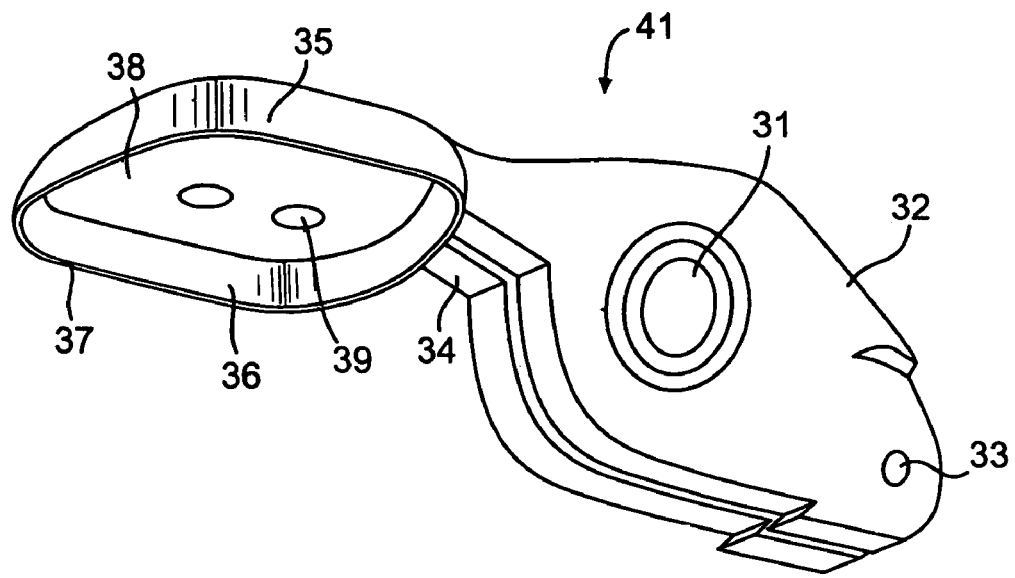
FIG. 4A is a perspective view of a molded portion of the upper jaw assembly of the forceps and collection assembly of FIG. 1.
Figure 4B:
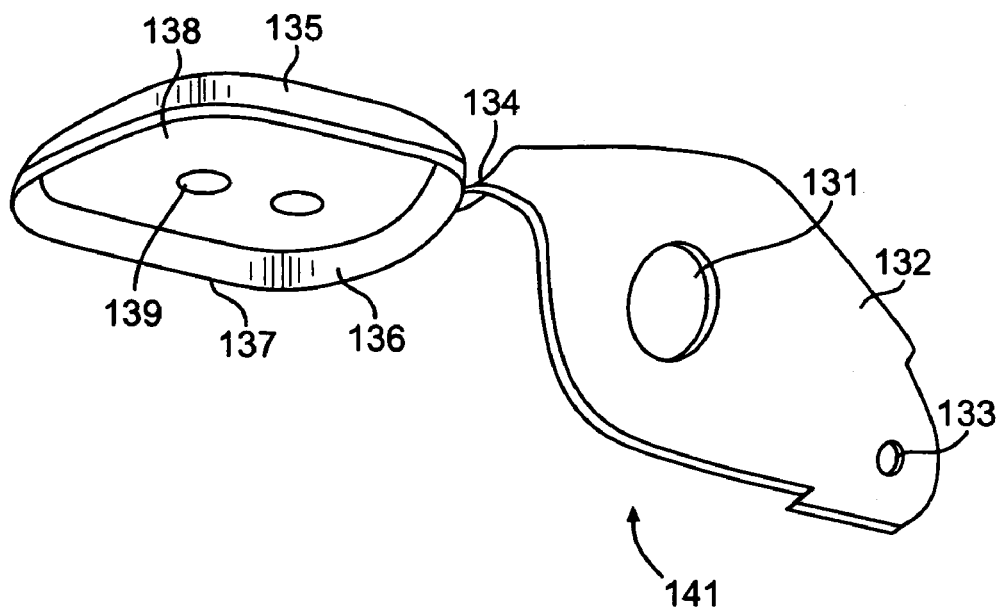
FIG. 4B is a perspective view of an insert portion of the upper jaw assembly of the forceps and collection assembly of FIG. 1.
Figure 5:
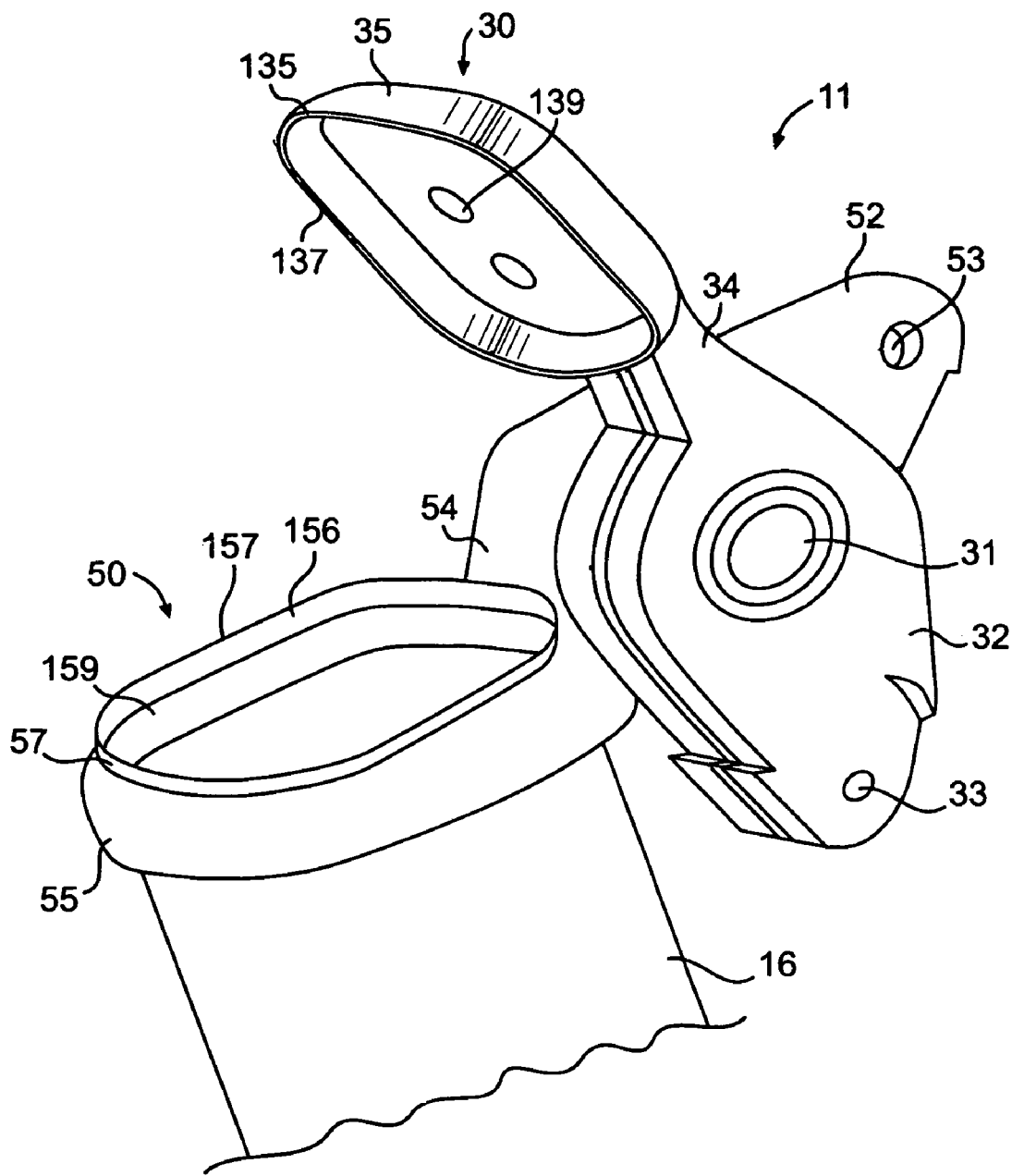
FIG. 5 is a perspective view of a jaw assembly of a forceps and collection assembly according to another embodiment of the present invention.
Figure 6:
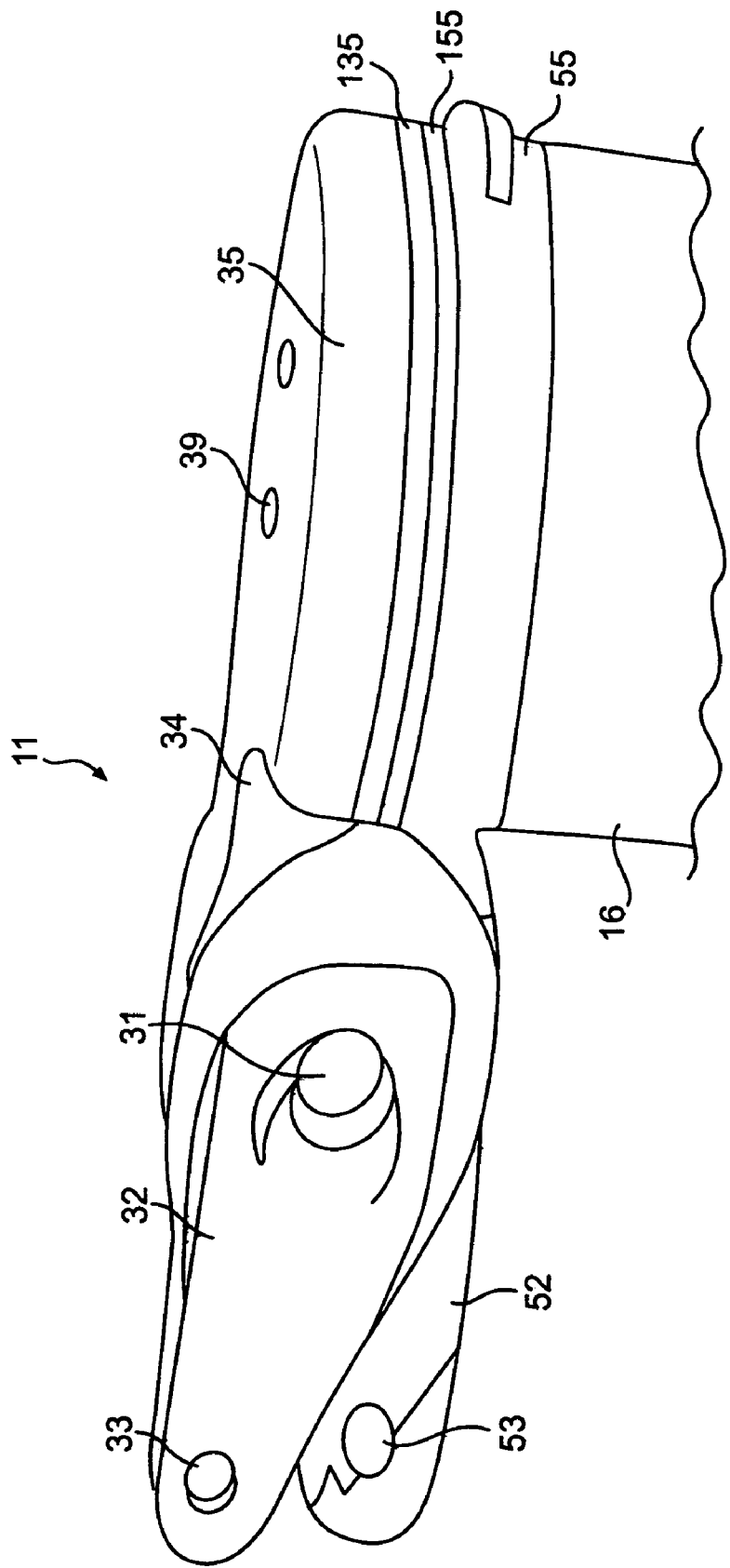
FIG. 6 is a perspective view of the jaw assembly of the forceps and collection assembly of FIG. 1 in a closed position.

An embodiment of the upper forceps assembly can be a one-piece integral assembly, such as a one-piece jaw that mates with the lower forceps assembly for cutting a tissue sample. Alternatively, the upper forceps assembly can also have multiple components. An embodiment of such an upper forceps assembly 30 is depicted in FIGS. 4A-4B and FIG. 5. Upper forceps assembly 30 has an upper molded portion 41 and a upper insert portion 141.

As shown in FIG. 4A, upper molded portion 41 has a pivot bore 31 on the central part of its tang portion 32 that is configured to accommodate pivot pin 19 of clevis 17. Tang portion 32 includes a pull wire hole 33 on its proximal end configured to receive and retain an actuating pull wire 14 that extends from proximal actuation handle 9. Upper molded portion 41 also has central bridging portion 34 that connects the proximal tang portion 32 to a cutting edge accommodating portion 35. Portion 35 and its cutting edge interface 37 are configured to oppose cutting portion 55 and its cutting edge interface 57 of lower molded portion 61 when brought together. Cutting edge interface 37 extends around substantially the edge of a bottom part 36 and is configured to accommodate and retain cutting edge 135 of the insert portion 141. Substantially adjacent to the inner portion of cutting edge interface 37 of upper forceps assembly 30 is oval protrusion 38. Oval protrusion 38 aids in pushing samples into pouch 16 of lower forceps assembly 50 once the tissue sample has been cut from the tissue tract. On an inner portion of oval protrusion 38 are circular-shaped ventilating holes 39 to assist in preventing biopsy samples from being stuck on bottom portion 36 of cutting portion 35 by minimizing the surface area that samples may stick to upper forceps assembly 30.

As depicted in the embodiment shown in FIG. 4B, upper insert portion 141 is shaped and configured similar to upper molded portion 61 so that it may be inserted and retained therein. Upper insert portion 141 has a pivot bore 131 on the central part of a tang portion 132 that is configured to accommodate pivot pin 19 of clevis 17. By having the pivot pin 19 extend through the pivot bores of the respective parts of the upper and lower forceps assemblies, those assemblies can rotate about pivot pin 19 with respect to each other. Tang portion 132 includes a pull wire hole 133 on its proximal end configured to mate with hole 33 and receive and retain the actuating pull wires 14 that also is received by hole 33. Upper insert portion 141 also has central bridging portion 134 that connects the tang portion 132 to cutting edge portion 135. Bridging portion 134 may have any number of planar or non-planar configurations. For example, bridging portion 134 may twist by transitioning from a substantially vertical orientation on the end connected to the tang portion 132, to a substantially horizontal orientation on the end connected to the cutting edge portion 135. As another example, bridging portion 134 may be substantially vertical and have a curved and/or S-shaped configuration between the tank portion and the cutting edge portion 135. Cutting edge portion 135 is sharp for cutting tissue portions from the tissue tract.

Upper insert portion 141 of upper forceps assembly 30 has a cutting portion 135 that includes a straight cutting edge 137 around its bottom 136. Cutting edge 135 is configured to extend past cutting edge interface 37 on molded portion 41. Substantially adjacent to the inner portion of straight cutting edge 137 is an oval protrusion 138. Oval protrusion 138 mates with protrusion 38 to aid in pushing samples into pouch 16 of lower forceps assembly 50 once the tissue sample has been cut from the tissue tract. Protrusion 138 includes circular-shaped ventilating holes 139 that mate with holes 39 to assist in preventing biopsy samples from being stuck on bottom 136 of cutting portion 135 by minimizing the surface area that samples may stick to upper forceps assembly 30.

Figure 8A:
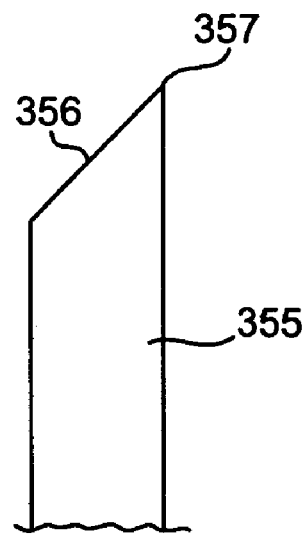
FIG. 8A is a cross-sectional view of a cutting portion of the insert portion of FIG. 2A
Figure 8B:
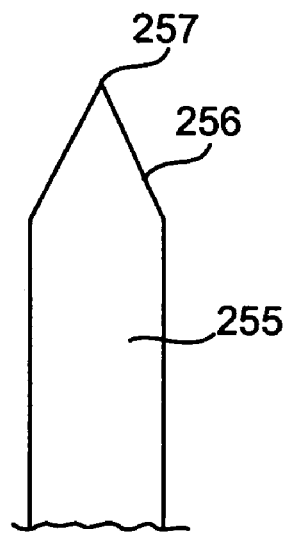
FIG. 8B is a cross-sectional view of a cutting portion of an insert portion according to another embodiment of the present invention.
Figure 8C:
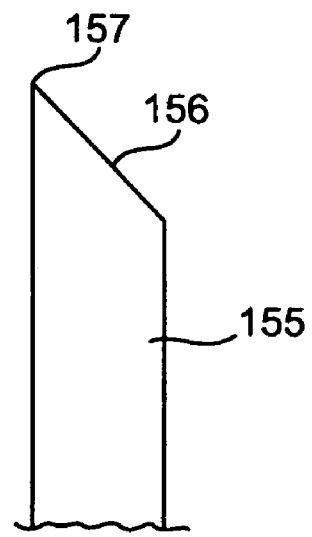
FIG. 8C is a cross-sectional view of a cutting portion of an insert portion according to another embodiment of the present invention.

Cutting edges 135, 155 of insert portions 141, 161 may have various configurations, as shown in FIGS. 8A-8C. For example, cutting edge 155 of insert portion 161 may have a beveled configuration as shown in FIG. 8C. There, straight cutting edge 157 is along the outer surface of cutting edge 155 and then the top part 156 of the cutting edge 155 slopes downward toward the inner surface of cutting edge 155. Alternatively, a cutting edge 255 may have its straight cutting edge 257 somewhere in between its inner and outer surfaces as shown in FIG. 8B, thus creating two top parts 256. As a further alternative, a cutting edge 355 may have its straight cutting edge 357 on the inner surface, from which top part 356 slopes down toward the outer surface of cutting edge 355, as shown in FIG. 8A. The cutting edge 135 of insert portion 141 may also have any of these or other suitable configurations.

Insert portions 141, 161 may be injection molded within molded portions 41, 61, for example, as shown in FIG. 5. More specifically, insert portions 141, 161 may be cut and/or stamped from a sheet of metal (for example, aluminum, stainless steel, etc.) using a conventional method of stamping known in the art. Alternatively, insert portions 141, 161 may also be cast from a mold or a die. The cutting edges 137, 157 may also be coined in to decrease metal thickness and achieve a sharp edge. Insert portions 141, 161 may then be placed in respective injection molds configured to accommodate insert portions 141, 161, and also configured to form the shape of molded portions 41, 61. Once insert portions 141, 161 have been positioned in their respective injection molds, plastic, rubber, or any other material suitable for injection molding may be injected into the injection mold. Once the material has adequately solidified, insert portions 141, 161 with their respective molded portions 41, 61 formed around them may be ejected from the ejection mold. In this state, cutting edge portions 137, 157 of insert portions 141, 161 are not covered by molded portions 41, 61.

Figure 3A:
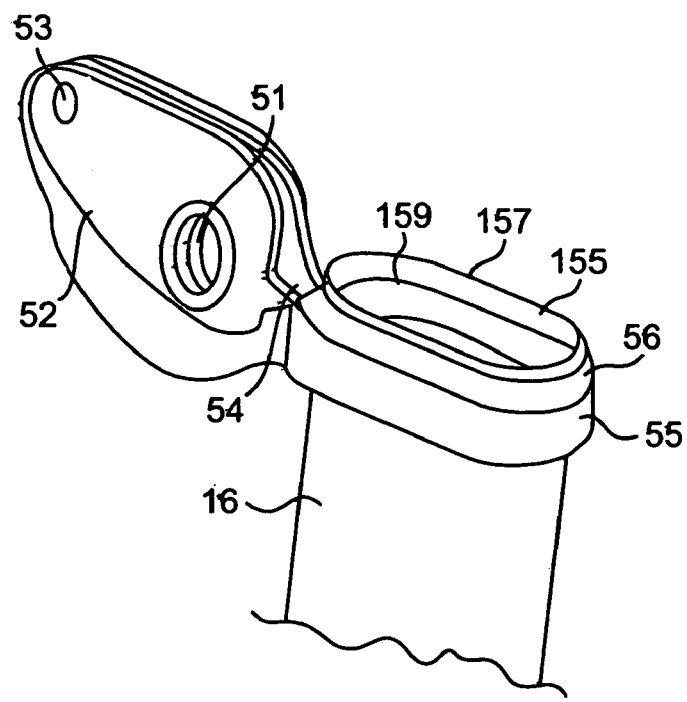
FIG. 3A is a perspective view of the lower jaw assembly of the forceps and collection assembly of FIG. 1.
Figure 3B:
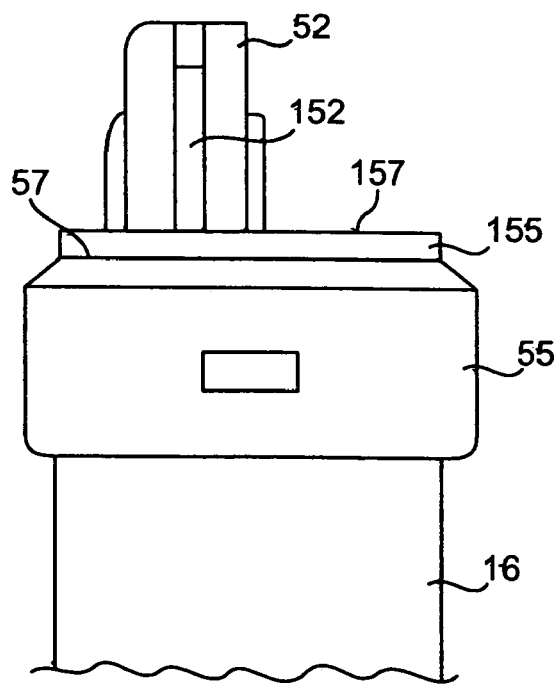
FIG. 3B is a schematic end view of the lower jaw assembly of the forceps and collection assembly of FIG. 1.
Figure 4C:
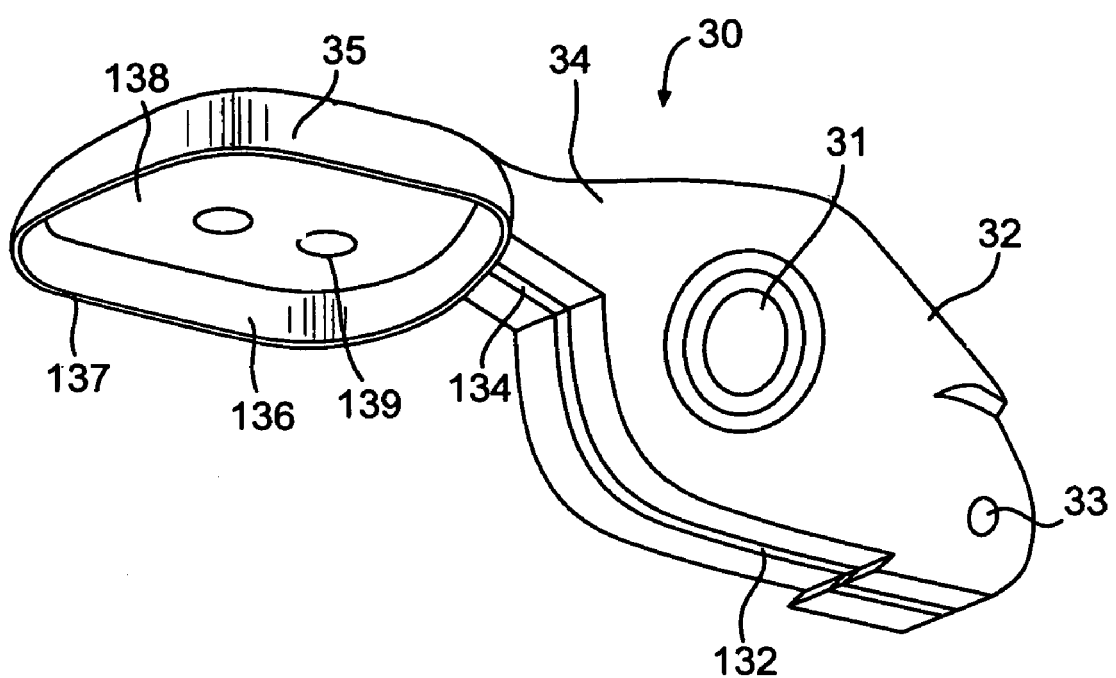
FIG. 4C is a perspective view of the upper jaw assembly of the forceps and collection assembly of FIG. 1.

Insert portions 141, 161 may also be inserted into molded portions 41, 61, for example, as shown in FIGS. 3A-3B and 4C. More specifically, insert portions 141, 161 may be formed substantially as set forth above. Molded portions 41, 61 may then be formed separately from insert portions 141, 161, for example, by injection molding molds configured to produce molded portions 41, 61. Once molded portions 41, 61 have been formed, insert portions 141, 161 may then be inserted into and joined together with molded portions 41, 61.

Molded portion 61 of lower forceps assembly 50 may have a vertical gap 252 that begins on the top of tang portion 52 and bridging portion 54 and extends substantially through the molded portion 61. The vertical gap 252 may be configured to receive tang portion 152 and bridging portion 154 of insert portion 161. The portion of the vertical gap 252 on the bridging portion 54 may be configured to accommodate a bridging portion 154 of the insert portion 161. For example, if the bridging portion 154 is in a twisted configuration, the vertical gap 252 may widen in width between the tang portion 52 and cutting portion 55. In another example, if the bridging portion 154 is in a curved and/or S-shaped configuration, the vertical gap 252 may have a matching curved and/or S-shaped configuration. Vertical wall 59 of molded portion 61 may also include a gap or slit so that, at the same time tang portion 52 and bridging portion 54 are placed in the vertical gap 252, vertical wall 159 of insert portion 161 may be placed within vertical wall 59 of molded portion 61, and both vertical walls 59, 159 may be configured such that they slightly interfere with each other and form a snug fit. Molded portion 61 and insert portion 161 may both be configured to prevent, especially when acquiring tissue samples, vertical wall 159 from substantially moving relative to vertical wall 59. For example, the fit between the vertical walls 59, 159 may be sufficient to prevent such movement. In another example, holding ring 60 located near the bottom of molded portion 61 may receive protrusion 160 also located near the bottom of insert portion 161 to prevent such movement. In yet another example, inner bottom part of vertical wall 59 may have a lip portion configured to receive and retain the bottom edge of vertical wall 159.

Molded portion 41 of upper forceps assembly 30 may have a vertical gap 232 that begins on the bottom of tang portion 32 and bridging portion 34 and extends substantially through the molded portion 41. The vertical gap 232 may be configured to receive tang portion 132 and bridging portion 134 of insert portion 141. The portion of the vertical gap 232 on the bridging portion 34 may be configured to accommodate a bridging portion 134 of the insert portion 141. For example, if the bridging portion 134 is in a twisted configuration, the vertical gap 232 may widen in width between the tang portion 32 and cutting portion 35. In another example, if the bridging portion 134 is in a curved and/or S-shaped configuration, the vertical gap 232 may have a matching curved and/or S-shaped configuration. Bottom part 36 of molded portion 41 may also include a gap or slit, so that, at the same time tang portion 32 and bridging portion 34 are placed in the vertical gap 232, bottom part 136 of insert portion 141 may be placed within bottom part 36 of molded portion 41, and the inner and/or outer edges of both bottom parts 36, 136 may be configured such that they slightly interfere with each other and form a snug fit. In this state, the upper forceps assembly 30 has a top portion which is plastic from the molded portion 41, and a bottom part 136 which is metal from the insert portion 141.

In other embodiments, forceps and collection assembly 10 may have various alternate configurations. For example, clevis 17 may be any connector configured to couple distal end effector assembly 11 to tubular member 12. In addition, instead of pull wires 14, assembly 10 may include any components suitable for connection to and actuation of the distal end effector assembly 11 or any other distal end effector assembly. Accordingly, upper forceps assembly 30 and lower forceps assembly 50 need not have pull wire holes, but instead may have components configured to interface with any actuation assembly known in the art. Cutting portions 135, 155 of upper and lower forceps assemblies 30, 50 need not be straight edge, but may have serrations, teeth, or any other cutting configuration that can cut tissue portions when brought together and/or hold the tissue portions in place. In addition, the cutting portion 135 and/or cutting edge 137 of the upper forceps assembly 30 need not be sharp at all, and instead may be flat or not otherwise sharp. In such a configuration, the cutting portion 135 provides a surface against which the cutting portion 155 and/or sharp cutting edge 157 of the lower forceps assembly 50 mates with to cut tissue.

In various embodiments, portions of the forceps and collection assembly 10 may be made of different materials. Molded portions 41, 61 may be made of a biocompatible plastic or other material suitable for accommodating and retaining their inserts. For example, molded portions 41, 61 may be formed from polycarbonate, PEEK, Nylon, or any other suitable material. In selecting a material, several factors may come into consideration, for example, the desired hardness as determined by a durometer.

Insert portions 141, 161 may be made of a biocompatible metal or any other material suitable for cutting tissue, and may have various thicknesses or configurations, such as a mesh type configuration. Examples of various materials suitable for portions 141, 161 include metals (stainless steel, brass, aluminum, cooper, nitinol), composites, plastics, ceramics, glass, Kevlar fibers, and carbons. Insert portions 141, 161 may also have rigid and/or non-rigid portions. In yet another example, the sharpness of cutting edges 137, 157 of cutting portions 135, 155 may vary along its circumference (e.g., some portions of cutting edges 137, 157 may be sharper than other portions of cutting edges 137, 157). Cutting portions 135, 155 may be connected to a source of current and heated (e.g., monopolar or bi-polar) to perform electrocautery, and may have different finishes. For example, they may be plated, coated, and/or have a stick or non-stick substance adhering to its surface.

In other embodiments, an end effector assembly having insert portions 141, 161 having cutting edges 137, 157 or other manipulator edges/surfaces either molded or inserted into a molded portion can be used in other medical or non-medical devices, for example, graspers, scissors, separators, forceps, vein strippers, retractors, and trocars.

In other embodiments, pouch 16 may have various alternate configurations. For example, pouch 16 may have other shapes and may be composed of any suitable biocompatible material. Pouch 16 may be composed of a material and/or have a wall thickness that allows a desired amount of flexibility and/or compression of pouch 16. For example, if the biopsy samples are especially sensitive, pouch 16 may be configured to be more rigid such that it does not bend or compress as much when it comes into contact with either a tissue tract wall or parts of an endoscope, such as a seal. Flush adapter interface 79 need not have an hourglass shape, as any configuration that can be coupled to a flush adapter or other tissue sample removal device while also preventing biopsy samples from exiting central cavity 75 through flush adapter interface 79 is also contemplated. In addition, pouch 16 may be integrally formed with lower jaw 50 as a single piece.

In other embodiments, forceps and collection assembly 10 and the accompanying mechanisms described above may be used with any medical or non-medical procedure, such as endoscopy, urology, gynecology, neurology, and oncology. In addition, each of forceps and collection assembly 10, or its subcomponents thereof, may be used independently of each other, each being individually configured to be used with other similar but not necessarily identical parts. For example, the insert portions 141, 161 may be used independently of the molded portions 41, 61.

A method of using forceps and collection assembly 10 in connection with an endoscopic biopsy procedure will now be described. An endoscope with a working channel first is placed into the body, for example, a tissue tract, using a method known in the art. Forceps and collection assembly 10 then is inserted into the working channel of the endoscope to the endoscope distal end. During insertion, upper forceps assembly 30 and lower forceps assembly 50 are closed.

Distal end effector assembly 11 then is advanced to the desirable tissue portion or portions and actuated. Specifically, once upper forceps assembly 30 and lower forceps assembly 50 are positioned proximate the tissue portion from which a sample is desired, the user actuates a handle portion and upper forceps assembly 30 and lower forceps assembly 50 are opened (i.e. they are separated). For example, pull wires 14 are advanced distally and push on pull wire holes 33, 53, 133, 153 on tang portions 32, 52, 132, 152. The pushing causes tang portions 32, 52, 132, 152 of upper forceps assembly 30 and lower forceps assembly 50 to rotate away from each other and thus cause upper forceps assembly 30 and lower forceps assembly 50 to open. Pull wires 14 may be advanced distally using any method known in the art, for example, by pushing on a spool portion of a handle.

Once upper and lower forceps assemblies 30, 50 are open, forceps and collection assembly 10 is advanced to the desired tissue and upper and lower forceps assemblies 30, 50 are closed. For example, pull wires 14 are retracted proximally, pulling on pull wire holes 33, 53, 133, 153 of tang portions 32, 52, 132, 152. The pulling causes tang portions 32, 52, 132, 152 to rotate toward each other and cause upper and lower forceps assemblies 30, 50 to close. While upper and lower forceps assemblies 30, 50 close, a sample of tissue is caught between upper forceps assembly 30 and lower forceps assembly 50. Cutting edges 137, 157 of upper forceps assembly 30 and lower forceps assembly 50 then interact and cause a biopsy sample to be cut from the tissue tract. As upper and lower forceps assemblies 30, 50 close, oval protrusion 38 aids in pushing the biopsy sample into central hole 58 of lower forceps assembly 50 and into passage 73 past front rim 71 of pouch 16, and into central cavity 75 of pouch container 74. Central hole 58, passage 73, central cavity 75, and passage 78 and its open bottom may be substantially axially aligned with each other.

Once in central cavity 75 of pouch container 74, the biopsy samples should fall toward flush adapter interface end 79 of pouch 16. However, even if they initially do not, acquisition of further samples by the upper and lower forceps assemblies 30, 50 should push the biopsy samples already in central cavity 75 further from front rim 71 and base wall 72. To prevent biopsy samples from getting stuck in central cavity 75 and impeding the acquisition of further biopsy samples, ventilation holes 76 assist in preventing such sticking by reducing the surface area on which the tissue samples can stick, thus facilitating the movement of the biopsy samples toward flush adapter interface end 79. As flush hole 78 is too narrow for biopsy samples cut by forceps 15 to pass, the biopsy samples are stored in pouch container 74 between flush adapter interface 79 and front rim 71 until removal.

Once the biopsy sample is stored in pouch 16, distal end effector assembly 11 may be advanced to additional tissue tract portions where a biopsy sample may be desired, and the biopsy samples may be taken using the method substantially as set forth above. These steps may be repeated as many times as desired until either the user decides to cease acquisition of further biopsy samples or central cavity 75 of pouch container 74 reaches its maximum capacity.

Once the user decides that enough biopsy samples have been acquired during a single pass, assembly 10 is retracted out of the tissue tract and the working channel of the endoscope. Specifically, with upper and lower forceps assemblies 30, 50 in a closed position, forceps and collection assembly 10 is retracted back out of the endoscope working channel.

Once assembly 10 is retracted out of the endoscope, the biopsy samples are removed from pouch 16. Any suitable method removing the biopsy samples from the pouch 16 is acceptable, including those described in U.S. patent application Ser. No. 10/658,261 filed Sep. 10, 2003, and entitled "A FORCEPS AND COLLECTION ASSEMBLY WITH ACCOMPANYING MECHANISMS AND RELATED METHODS OF USE," mentioned above and incorporated herein by reference. From there, the biopsy samples will be taken away for analysis or any other type of desired procedure. The endoscope may be withdrawn from the body before or after removal of samples from pouch 16.

In the various embodiments, any suitable method of viewing the procedure known in the art is contemplated, for example, the use of the endoscope lens or other electronic methods of viewing endoscopic procedures that are known in the art.

In other embodiments, there may be various alternate method steps that may be executed. For example, upper and lower forceps assemblies 30, 50 may be individually actuated (i.e. only one jaw moves to open and close the assembly 11) and/or one jaw may be stationary and the other movable.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An end effector assembly for obtaining multiple tissue samples comprising:
    a first jaw; and
    a jaw assembly pivotally connected to the first jaw and having:
        a cutting portion for mating with the first jaw to cut a tissue sample;
        a holder; and
        a storage portion configured to store tissue samples,
        wherein the holder is configured to receive the cutting portion and the storage portion,
        wherein the holder has a groove for receiving both a protrusion on the cutting portion and a protrusion on the storage portion.

2. The device of claim 1, wherein the holder has a top configured to receive the cutting portion and a bottom configured to receive the storage portion.

3. The device of claim 1, wherein at least a portion of the storage portion and a portion of the cutting portion are press-fit into the holder.

4. The device of claim 1, wherein the cutting portion and the holder are comprised of different materials.

5. The device of claim 1, wherein the cutting portion is comprised of metal and the holder is comprised of a non-metal material.

6. The device of claim 5, wherein the non-metal material is at least one of plastic, rubber, polycarbonate, PEEK, and Nylon.

7. The device of claim 1, wherein the cutting portion and the holder are comprised of the same material.

8. The device of claim 1, wherein the first jaw includes a holder and a cutting portion.

9. The device of claim 1, wherein the holder and the cutting portion are formed separately.

10. The device of claim 1, wherein the holder is formed around the cutting portion.

11. The device of claim 1, wherein the storage portion is a pouch.

12. The device of claim 1, wherein the cutting portion has a non-straight portion connecting a tang to a cutting edge and configured to be received in a correspondingly-shaped gap in the holder.

13. The device of claim 12, wherein the tang defines a pivot bore and an actuator hole, and the non-straight portion is between the tang and the cutting edge.

14. The device of claim 1, wherein the cutting portion includes a cutting edge opposing a cutting surface of the first jaw.

15. The device of claim 1, wherein the cutting portion is stamped.

16. The device of claim 1, wherein the holder is injection molded.

17. The device of claim 1, wherein the cutting portion inserts into the holder.

18. The device of claim 1, wherein at least a portion of the cutting portion extends from the holder.

19. The device of claim 1, wherein the cutting portion is configured to provide structural support to the holder.

20. The device of claim 1, wherein a sharp portion of the first jaw mates with the cutting portion to cut the tissue sample.

21. The device of claim 1, wherein a sharp portion of the cutting portion mates with the first jaw to cut the tissue sample.

22. The device of claim 1, wherein a sharp portion of the first jaw mates with a sharp portion of the cutting portion to cut the tissue sample.

23. The device of claim 1, wherein the protrusion on the cutting portion extends continuously about an entire perimeter of a bottom edge of a vertical wall of the cutting portion.

24. The device of claim 1, wherein the groove is located closer to a bottom of the holder than a top of the holder.

25. An end effector assembly for obtaining multiple tissue samples comprising:
a first jaw; and
a jaw assembly pivotally connected to the first jaw and having:
a cutting portion for mating with the first jaw to cut a tissue sample;
a holder; and
a storage portion configured to store tissue samples, wherein the holder is configured to receive the cutting portion and the storage portion,
wherein the holder has a groove for receiving both a protrusion on the cutting portion and a protrusion on the storage portion, wherein both the cutting portion and the holder are comprised of metal.

26. An endoscopic instrument comprising:
a proximal handle coupled to a distal end effector assembly via an elongate member, the proximal handle for actuating the distal end effector assembly;
wherein the distal end effector assembly includes:
a first jaw; and
a jaw assembly pivotally connected to the first jaw and having:
a cutting portion for mating with the first jaw to cut a tissue sample;
a holder; and
a storage portion configured to store tissue samples, wherein the holder is configured to receive the cutting portion and the storage portion,
wherein the holder has a groove for receiving both a protrusion on the cutting portion and a protrusion on the storage portion.

27. The device of claim 26, wherein the holder has a top configured to receive the cutting portion and a bottom configured to receive the storage portion.

28. The device of claim 26, wherein the cutting portion and the holder are composed of different materials.

29. The device of claim 26, wherein the cutting portion is comprised of metal and the holder is comprised of a non-metal material.

30. The device of claim 29, wherein the non-metal material is at least one of plastic, rubber, polycarbonate, PEEK, and Nylon.

31. The device of claim 26, wherein the cutting portion and the holder are comprised of the same material.

32. The device of claim 26, wherein the first jaw includes a holder and a cutting portion.

33. The device of claim 26, wherein the holder and the cutting portion are formed separately.

34. The device of claim 26, wherein the holder is formed around the cutting portion.

35. The device of claim 26, wherein the storage portion is a pouch.

36. The device of claim 26, wherein the cutting portion has a non-straight portion connecting a tang to a cutting edge and configured to be received in a correspondingly-shaped gap in the holder.

37. The device of claim 36, wherein the tang defines a pivot bore and an actuator hole, and the non-straight portion is between the tang and the cutting edge.

38. The device of claim 26, wherein the cutting portion includes a cutting edge opposing a cutting surface of the first jaw.

39. The device of claim 26, wherein the cutting portion is stamped.

40. The device of claim 26, wherein the holder is injection molded.

41. The device of claim 26, wherein the cutting portion inserts into the holder.

42. The device of claim 26, wherein at least a portion of the cutting portion extends from the holder.

43. The device of claim 26, wherein the cutting portion is configured to provide structural support to the holder.

44. The device of claim 26, wherein a sharp portion of the first jaw mates with the cutting portion to cut the tissue sample.

45. The device of claim 26, wherein a sharp portion of the cutting portion mates with the first jaw to cut the tissue sample.

46. The device of claim 26, wherein a sharp portion of the first jaw mates with a sharp portion of the cutting portion to cut the tissue sample.

47. The device of claim 26, wherein the protrusion on the cutting portion extends continuously about an entire perimeter of a bottom edge of a vertical wall of the cutting portion.

48. The device of claim 26, wherein the groove is located closer to a bottom of the holder than a top of the holder.

49. An endoscopic instrument comprising:
- a proximal handle coupled to a distal end effector assembly via an elongate member, the proximal handle for actuating the distal end effector assembly;
- wherein the distal end effector assembly includes:
  - a first jaw; and
  - a jaw assembly pivotally connected to the first jaw and having:
    - a cutting portion for mating with the first jaw to cut a tissue sample;
    - a holder; and
    - a storage portion configured to store tissue samples,
    - wherein the holder is configured to receive the cutting portion and the storage portion,
- wherein the holder has a groove for receiving both a protrusion on the cutting portion and a protrusion on the storage portion, wherein both the cutting portion and the holder are comprised of metal.

* * * * *